(12) United States Patent
Uchida

(10) Patent No.: US 9,814,381 B2
(45) Date of Patent: Nov. 14, 2017

(54) OPHTHALMIC APPARATUS AND CONTROL METHOD THEREFOR, PERSONAL DIGITAL ASSISTANT DEVICE AND CONTROL METHOD THEREFOR, OPHTHALMIC SYSTEM, AND PROGRAM

(71) Applicant: CANON KABUSHIKI KAISHA, Tokyo (JP)

(72) Inventor: Koji Uchida, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/145,710

(22) Filed: May 3, 2016

(65) Prior Publication Data

US 2016/0338583 A1 Nov. 24, 2016

(30) Foreign Application Priority Data

May 20, 2015 (JP) ................................. 2015-102838

(51) Int. Cl.
*A61B 3/14* (2006.01)
*A61B 3/00* (2006.01)
*A61B 3/15* (2006.01)
*A61B 3/18* (2006.01)
*A61B 5/00* (2006.01)

(52) U.S. Cl.
CPC ............ *A61B 3/0025* (2013.01); *A61B 3/005* (2013.01); *A61B 3/145* (2013.01); *A61B 3/152* (2013.01); *A61B 3/18* (2013.01); *A61B 5/002* (2013.01)

(58) Field of Classification Search
USPC .................................................. 351/200–246
See application file for complete search history.

(56) References Cited

U.S. PATENT DOCUMENTS 8,899,748 B1 * 12/2014 Migdal .................... A61B 3/14
351/206
2010/0033676 A1 * 2/2010 De Vries ................ A61B 3/102
351/206

FOREIGN PATENT DOCUMENTS

JP 2014-104130 A 6/2014

* cited by examiner

*Primary Examiner* — Mohammed Hasan
(74) *Attorney, Agent, or Firm* — Canon U.S.A., Inc. IP Division

(57) ABSTRACT

An ophthalmic apparatus is capable of communicating with a PDA device provided with a display unit and includes a main body that includes an image-capturing unit, the image-capturing unit obtaining a moving image of an eye to be examined (target eye) based on light returned from the target eye which is illuminated, the moving image of the target eye used by the ophthalmic apparatus for obtaining, based on an examination of the target eye, information regarding the target eye, a driving unit that drives the main body, a transmission unit that transmits, before the information regarding the target eye is obtained, a moving image signal of the obtained moving image to the PDA device, a reception unit that receives a control signal from the PDA device during transmission of the moving image signal, and a control unit that controls the driving unit based on the received control signal.

20 Claims, 8 Drawing Sheets

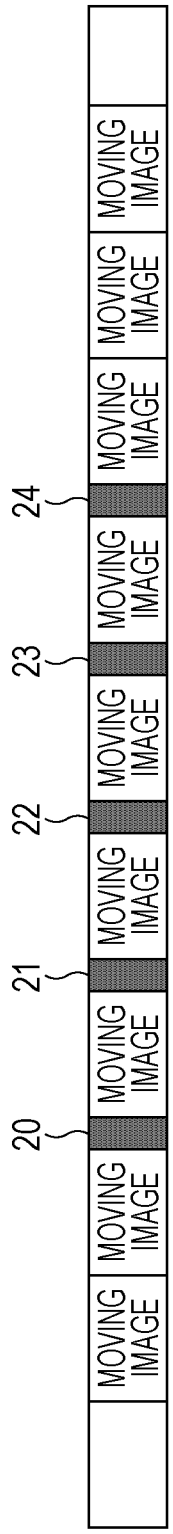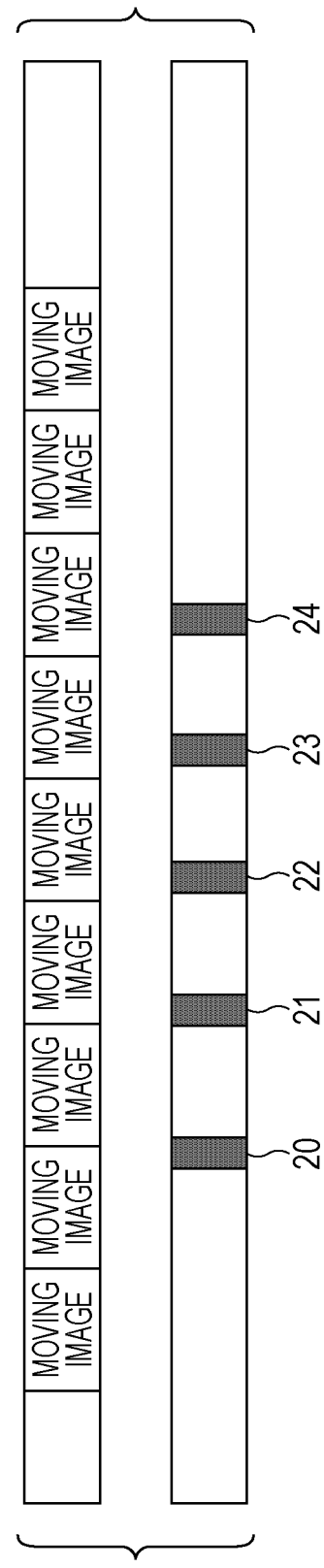

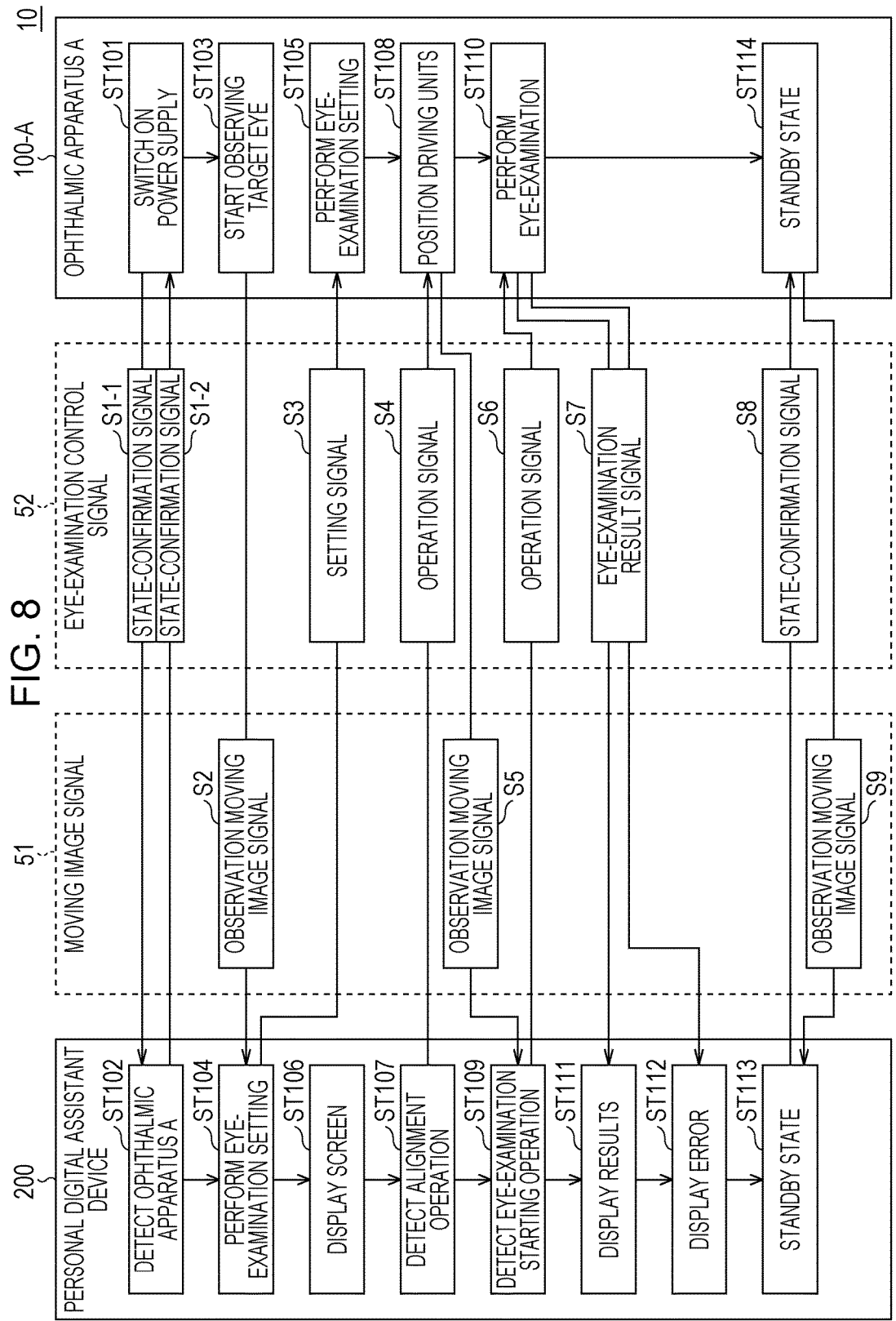

OPHTHALMIC APPARATUS AND CONTROL METHOD THEREFOR, PERSONAL DIGITAL ASSISTANT DEVICE AND CONTROL METHOD THEREFOR, OPHTHALMIC SYSTEM, AND PROGRAM

BACKGROUND OF THE INVENTION

Field of the Invention

The present invention relates to an ophthalmic apparatus that is used for examining an eye to be examined, a method of controlling the ophthalmic apparatus, a personal digital assistant device that is configured to be capable of wirelessly communicating with the ophthalmic apparatus, a method of controlling the personal digital assistant device, an ophthalmic system that includes the personal digital assistant device and the ophthalmic apparatus, and a program that causes a computer to perform control by the above control methods.

Description of the Related Art

In ophthalmologic diagnosis and treatment, there is a case where an examiner performs an operation for examining a patient's eye, which is to be examined, by using various ophthalmic apparatuses. In this case, a personal digital assistant (PDA) device is useful for checking information regarding patients and the like while, for example, the examiner is coming and going between an examination room, a waiting room, and the like. Japanese Patent Laid-Open No. 2014-104130 (hereinafter referred to as Patent Document 1) discloses an ophthalmic apparatus that is configured to be capable of communicating with a PDA device, such as a personal computer.

More specifically, Patent Document 1 discloses an ophthalmic apparatus that includes a main body used for acquiring information regarding an eye to be examined, a to-be-attached portion to which a PDA device having a communication function is to be attached, a communicating unit that performs telecommunication with the PDA device, and a main-body control unit that controls the main body on the basis of information input from the PDA device via the communicating unit.

In addition, Patent Document 1 discloses that a state where a mobile terminal has been mounted on the main body and a state where the mobile terminal has been removed from the main body are detected by using a microswitch or a (non-contact) integrated circuit (IC) card.

Furthermore, Patent Document 1 discloses that the main body that acquires information items regarding an eye to be examined (examination results of the eye to be examined and a captured image of the eye to be examined) is controlled on the basis of information items (operation-condition information items) input from a mobile terminal via a communication interface, the operation-condition information items including fixation-position information items from an optical coherence tomography (OCT) apparatus and a fundus camera, an imaging-mode information item, and an information item indicating the light intensity of illuminating light.

Furthermore, Patent Document 1 discloses that the main body acquires information items regarding an eye to be examined and transmits the acquired information items regarding the eye to be examined to a mobile terminal.

SUMMARY OF THE INVENTION

An ophthalmic apparatus according to a first aspect of the present invention is capable of communicating with a personal digital assistant (PDA) device, the PDA device including a display unit, and includes a main body that includes an image-capturing unit, the image-capturing unit obtaining a moving image of an eye to be examined based on light returned from the eye to be examined which is illuminated, the moving image of the eye to be examined used by the ophthalmic apparatus for obtaining, based on an examination of the eye to be examined, information regarding the eye to be examined, a driving unit that drives the main body, a transmission unit that transmits, before the information regarding the eye to be examined is obtained, a moving image signal of the obtained moving image to the PDA device, a reception unit that receives a control signal from the PDA device during transmission of the moving image signal, and a control unit that controls the driving unit based on the received control signal.

A personal digital assistant (PDA) device according to a second aspect of the present invention is capable of communicating with an ophthalmic apparatus and includes a display unit, a reception unit that receives, from the ophthalmic apparatus, a moving image of an eye to be examined, the moving image being obtained by an image-capturing unit based on light returned from the eye to be examined which is illuminated, a display control unit that causes the display unit to display the received moving image and a transmission unit that transmits a control signal to the ophthalmic apparatus based on an instruction issued on the displayed moving image.

In addition, the present invention includes an ophthalmic system that includes the above-described ophthalmic apparatus and the above-described PDA device, a method of controlling the above-described ophthalmic apparatus, a method of controlling the above-described PDA device, and a program that causes a computer to perform control by the above control methods.

Further features of the present invention will become apparent from the following description of exemplary embodiments with reference to the attached drawings.

BRIEF DESCRIPTION OF THE DRAWINGS

FIGS. 3A and 3B are diagrams each schematically illustrating an example of a transmission signal that is to be transmitted to the personal digital assistant device from a wireless transmission unit illustrated in FIG. 2.

FIG. 8 is a flowchart illustrating an exemplary process in a control method used in the ophthalmic system according to the embodiment of the present invention.

DESCRIPTION OF THE EMBODIMENTS

In the related art, information that can be viewed by using a personal digital assistant (PDA) device has not been appropriately changed in accordance with the usage state of an ophthalmic apparatus or the like. Conceivable examples of the usage state of such an ophthalmic apparatus may be the case where an eye examination is performed by using the ophthalmic apparatus and the case where an eye examination is not performed, and accordingly, the ophthalmic apparatus is not used. In these cases, conceivable display contents of a PDA device may be a screen related to the ophthalmic apparatus and a screen regarding awaiting patients (a screen for inputting patient information). In such a case, in the related art, these screens have not been suitably changed in accordance with the usage state of an ophthalmic apparatus. In other words, in the related art, when an examiner performs an eye examination on a patient's eye by using an ophthalmic apparatus while carrying a PDA device, the eye examination may not be performed with good efficiency.

Accordingly, an embodiment of the present invention has been made in view of the above problems and is directed at performing an eye examination with good efficiency when an examiner performs an eye examination on a patient's eye by using an ophthalmic apparatus while carrying a PDA device.

For example, since an eye to be examined moves with respect to an ophthalmic apparatus due to involuntary eye movement and the like, an alignment operation needs to be performed before acquiring information regarding the eye to be examined.

Thus, before acquiring information regarding the eye to be examined, it is required that the alignment operation be performed with good efficiency by using a PDA.

Accordingly, the ophthalmic apparatus according to an embodiment of the present invention transmits, before acquiring information regarding an eye to be examined, a moving image signal of an anterior eye portion to a PDA and receives a control signal for an alignment operation from the PDA.

Embodiments of the present invention will be described below with reference to the drawings.

Figure 1:
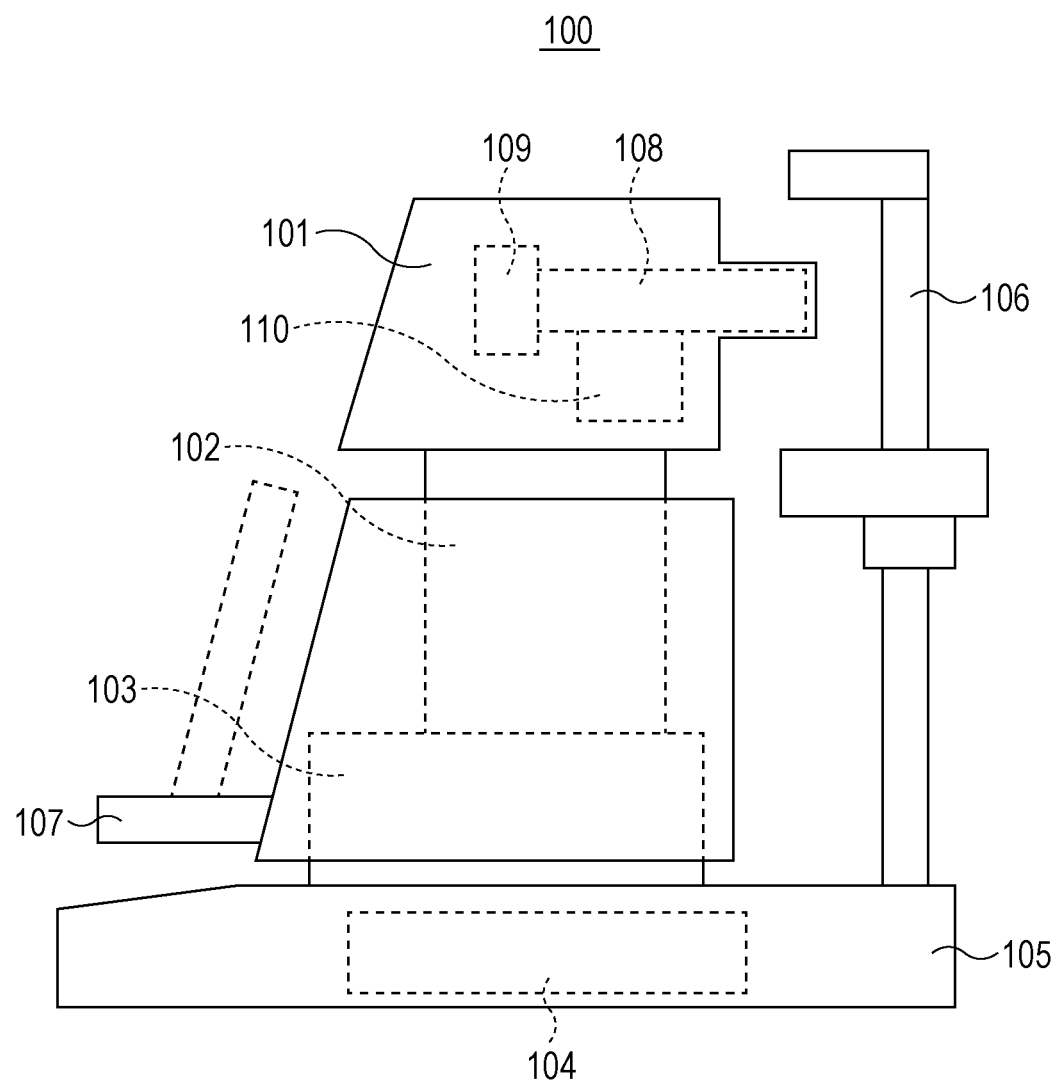
FIG. 1 is a diagram illustrating an exemplary appearance configuration of an ophthalmic apparatus according to an embodiment of the present invention.

FIG. 1 is a diagram illustrating an exemplary appearance configuration of an ophthalmic apparatus 100 according to an embodiment of the present invention.

An eye-examination unit 101 is disposed in an uppermost portion of the ophthalmic apparatus 100 illustrated in FIG. 1. The eye-examination unit 101 is an eye-examination unit that is used for examining a patient's (subject's) eye to be examined. Such an eye to be examined will hereinafter be referred to as a target eye.

A vertical driving unit 102 and a left-right-and-front-rear driving unit 103 that is capable of moving in a horizontal plane are disposed below the eye-examination unit 101. A base 105 that is equipped with a power supply unit 104 is disposed below the left-right-and-front-rear driving unit 103, and a face-receiving unit 106 with which a subject's face is to be fixed in place is disposed on the base 105 on a first side, the first side being the side of the base 105 that is closest to a subject. A rack 107 on which an examiner can place a personal digital assistant (PDA) device 200 in order to perform an eye-examination operation is disposed on a second side that is opposite to the first side of the base 105, the second side being the side of the base 105 that is closest to an examiner.

An observation optical system 108, an image-capturing unit 109, and an eye-examination optical system 110 are built into the eye-examination unit 101. The observation optical system 108 and the image-capturing unit 109 also serve as a detection unit that observes a target eye and positions the target eye. The eye-examination optical system 110 is used for performing examinations on a target eye, the examinations including fundus photography, eye refractive power measurement, intraocular pressure measurement, corneal endothelial photography, corneal thickness measurement, and axial length measurement.

Figure 2:
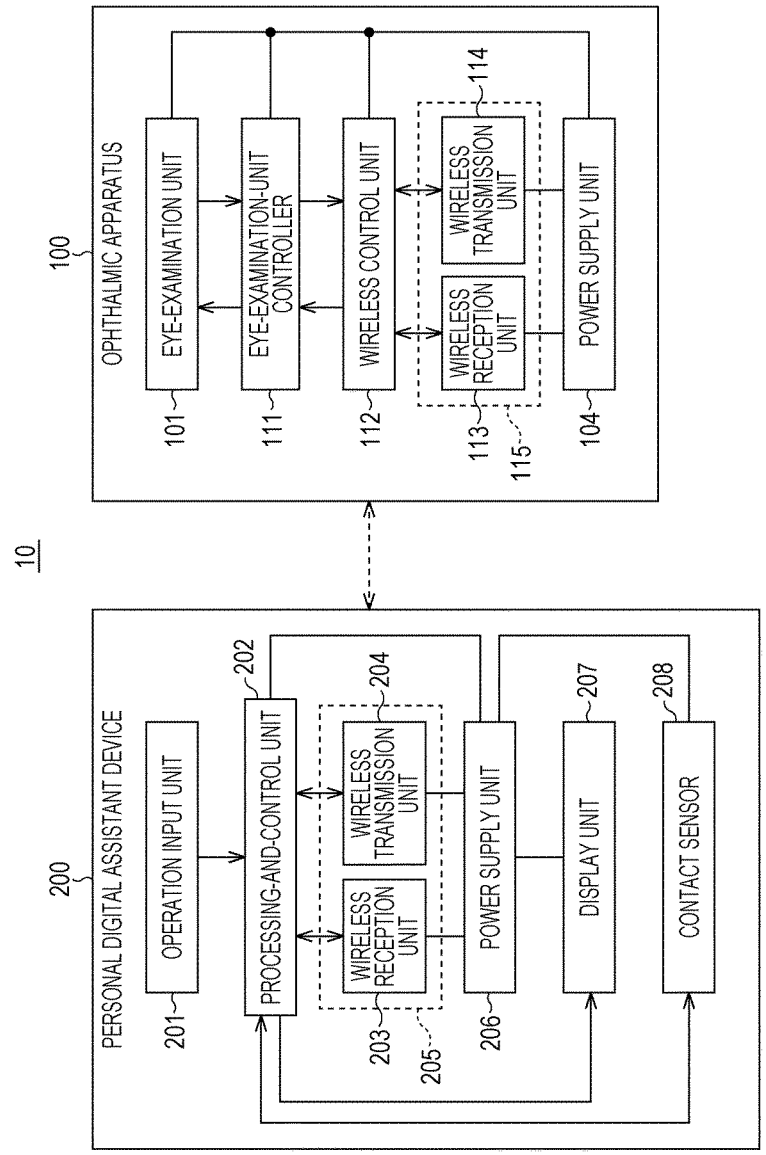
FIG. 2 is a diagram illustrating exemplary functional configurations of the ophthalmic apparatus and a personal digital assistant device that are included in an ophthalmic system according to the embodiment of the present invention.

FIG. 2 is a diagram illustrating exemplary functional configurations of the ophthalmic apparatus 100 and the PDA device 200 that are included in an ophthalmic system 10 according to the embodiment of the present invention. As illustrated in FIG. 2, the ophthalmic system 10 includes the ophthalmic apparatus 100 and the PDA device 200. Note that, in FIG. 2, elements similar to those illustrated in FIG. 1 are denoted by the same reference numerals.

The ophthalmic apparatus 100 is an apparatus used for examining a target eye and is configured to be capable of communicating with (capable of wirelessly communicating with) the PDA device 200. For example, as the ophthalmic apparatus 100 according to the present embodiment, an apparatus that includes a fundus camera, a scanning laser ophthalmoscope (SLO), a tonometer, a ref-ractometer, an optical coherence tomography (OCT) apparatus, and an adaptive optics (AO)-SLO or an apparatus that includes some of these optical systems, which are integrally formed with one another, can be employed. In this case, examinations to be performed on a target eye by using the ophthalmic apparatus 100 include "image capturing" operations using a fundus camera or an OCT apparatus. As illustrated in FIG. 2, the ophthalmic apparatus 100 includes the eye-examination unit 101, an eye-examination-unit controller 111, a wireless control unit 112, a wireless communicating unit 115, which includes a wireless reception unit 113 and a wireless transmission unit 114, and the power supply unit 104.

As described above, the eye-examination unit 101 is an eye-examination unit used for examining a patient's eye to be examined. In addition, as illustrated in FIG. 1, the observation optical system 108, the image-capturing unit 109, and the eye-examination optical system 110 are built into the eye-examination unit 101, and for example, a light source and a detection device each for use in an eye examination, a charge-coupled device (CCD) sensor, an actuator for use in an eye examination, and the like are disposed in the eye-examination unit 101. An eye-examination operation, which is performed by the eye-examination unit 101, is controlled on the basis of a control signal from the eye-examination-unit controller 111.

The eye-examination-unit controller 111 controls an eye-examination operation, which is performed by using the eye-examination unit 101, in accordance with information from the eye-examination unit 101, information from the wireless communicating unit 115, and the like. For example, the eye-examination-unit controller 111 performs control so as to drive the vertical driving unit 102 and the left-right-and-front-rear driving unit 103, which are illustrated in FIG. 1, in accordance with positioning information from the observation optical system 108, which is disposed in the eye-examination unit 101, so that a target eye can be automatically positioned. The eye-examination-unit controller 111 is electrically connected to the wireless control unit 112, and the eye-examination-unit controller 111 obtains information, which has been transmitted from the PDA device 200 and received by the wireless reception unit 113, and the like and transmits information and the like to the PDA device 200 by using the wireless transmission unit 114 via the wireless control unit 112.

The wireless control unit 112 controls a receiving operation performed by the wireless reception unit 113, which is included in the wireless communicating unit 115, and a transmitting operation performed by the wireless transmission unit 114, which is included in the wireless communicating unit 115.

The wireless communicating unit 115 wirelessly communicates with the PDA device 200 on the basis of a control signal from the wireless control unit 112 and includes the wireless reception unit 113 and the wireless transmission unit 114 as illustrated in FIG. 2.

For example, the wireless reception unit 113 receives, from the PDA device 200, a setting information item related to an examination (an eye examination) performed by using the eye-examination unit 101, a number-of-times information item related to the eye examination, an information item regarding an alignment operation performed by the eye-examination unit 101, an information item regarding an eye-examination starting operation related to the eye examination, and the like. Note that, in the present invention, the wireless reception unit 113 may be configured to receive at least one information item of these information items.

For example, the wireless transmission unit 114 transmits, in accordance with the positional relationship between the wireless transmission unit 114 and the PDA device 200, a moving-image signal of a target eye obtained as a result of an eye examination performed by using the eye-examination unit 101 and an eye-examination control signal related to the eye examination to the PDA device 200. For example, the wireless transmission unit 114 transmits the above-mentioned moving-image signal and the above-mentioned eye-examination control signal to the PDA device 200 in the following cases: the case where the ophthalmic apparatus 100 has been brought into contact with the PDA device 200 (e.g., the case where the eye-examination-unit controller 111 has detected, through a contact sensor (not illustrated) or the like, that the PDA device 200 had been placed on the rack 107 of the ophthalmic apparatus 100) and the case where the ophthalmic apparatus 100 is not in contact with the PDA device 200 and where the distance between the ophthalmic apparatus 100 and the PDA device 200 is smaller than a predetermined distance (e.g., the case where the wireless control unit 112 has detected that near field communication had been performed between the wireless communicating unit 115 and the PDA device 200 or the case where a circuit that is included in a wireless reception unit 203, which will be described later, (or the wireless reception unit 113) and that detects the distance between the ophthalmic apparatus 100 and the PDA device 200 has detected a distance smaller than a predetermined distance). In addition, the wireless transmission unit 114 transmits identification information that is used to identify the ophthalmic apparatus 100 to the PDA device 200.

An eye-examination control signal that is to be transmitted from the wireless transmission unit 114 to the PDA device 200 includes, for example, a set-value information item related to an examination (eye examination) to be performed by using the eye-examination unit 101, an eye-examination-mode-state information item related to the eye examination, an information item regarding left and right eyes each of which is a target eye, an information item regarding the presence or absence of an eye-examination error related to the eye examination, an eye-examination-result information item related to the eye examination (including a measured value, a captured still image, and the like). Note that, in the present invention, the eye-examination control signal may include at least one information item of these information items.

The wireless transmission unit 114 may transmit the above-mentioned moving-image signal to the PDA device 200 by using, for example, Bluetooth or a high-speed wireless local area network (LAN) communication standard. For example, for wireless communication of a moving-image signal, Bluetooth (Registered Trademark: IEEE802.15.1), which is a communication standard enabling high-speed (at a few tens of Mbps or greater) communication of an image of high image quality and radio wave communication within a distance range of about a few meters to about a few tens of meters, and high-speed wireless LAN communication standards (IEEE802.11n and IEEE802.11ac) each enabling wide-area radio wave communication of an image of ultrahigh image quality, are desirable.

In addition, the wireless transmission unit 114 may transmit the above-mentioned eye-examination control signal to the PDA device 200 by using, for example, a near field communication standard that uses a frequency band of 13.56 MHz. For example, for wireless communication of an eye-examination control signal, which includes an information item having a small size, a near field communication standard (ISO/IEC 18092) that enables communication only within a range of about a few centimeters to about one meter is desirable.

In the present embodiment, the wireless transmission unit 114 continuously transmits, from the ophthalmic apparatus 100 to the PDA device 200, a moving-image signal representing an observed state of a target eye and the above-mentioned eye-examination control signal at the same time. In addition, in the present embodiment, even in a state where the wireless transmission unit 114 is transmitting a moving-image signal to the PDA device 200, the wireless reception unit 113 receives, from the PDA device 200, a setting information item related to an examination (eye examination) to be performed by using the eye-examination unit 101, an information item regarding changing of an eye-examination mode state, an information item regarding an operation of positioning the eye-examination unit 101 with respect to a target eye, the operation being performed by an examiner, an emergency stop information item, and the like.

The power supply unit 104 supplies power to the eye-examination unit 101, the eye-examination-unit controller 111, the wireless control unit 112, the wireless reception unit 113, and the wireless transmission unit 114.

FIGS. 3A and 3B are diagrams each schematically illustrating an example of a transmission signal that is to be transmitted to the PDA device 200 from the wireless transmission unit 114 illustrated in FIG. 2.

FIG. 3A illustrates the configuration of a transmission signal in which information items of an eye-examination control signal are inserted between moving-image signals. In the example illustrated in FIG. 3A, the information items of the eye-examination control signal include a set-value information item 20 related to an eye examination, an eye-examination-mode-state information item 21 related to the eye examination, an information item 22 regarding left and right eyes each of which is a target eye, an information item 23 regarding the presence or absence of an eye-examination error related to the eye examination, and an eye-examination-result information item 24 related to the eye examination (including a measured value, a captured still image, and the like). In the transmission signal illustrated in FIG. 3A, the information items 20 to 24 of the eye-examination control signal are inserted between the moving-image signals at predetermined time intervals, so that two types of signals, which are a moving-image signal and an eye-examination control signal, can be transmitted. For example, in communication in accordance with the Bluetooth (Registered Trademark) communication standard, two types of signals, which are a moving-image signal and an eye-examination control signal, may be included in a transmission signal or, in high-speed wireless LAN communication, the two types of signals, which are a moving-image signal and an eye-examination control signal, may be included in a transmission signal.

FIG. 3B illustrates the configuration of a transmission signal when it is assumed that moving-image signals and information items of an eye-examination control signal are transmitted by using two different communication standards. For example, wireless communication of the moving-image signals is performed by using the Bluetooth (Registered Trademark), which is a communication standard enabling high-speed (at a few tens of Mbps or greater) communication or a high-speed wireless LAN communication standard. For example, wireless communication of the eye-examination control signal, which includes an information item having a small size, is performed by using a near field communication standard (ISO/IEC 18092).

Regarding a reception signal to be received by the wireless reception unit 113, during the period when the wireless transmission unit 114 is transmitting a transmission signal such as one of those illustrated in FIG. 3A and FIG. 3B, the wireless reception unit 113 can receive a setting information item related to an eye examination, an information item regarding changing of an eye-examination mode state, an information item regarding an operation performed on the eye-examination unit 101 by an examiner, an emergency stop information item, and the like.

The PDA device 200 will now be described.

The PDA device 200 is configured to be capable of communicating with (capable of wirelessly communicating with) at least one ophthalmic apparatus 100 used for examining a target eye. In other words, the PDA device 200 according to the present embodiment is configured to be capable of wirelessly communicating with a plurality of ophthalmic apparatuses 100.

As illustrated in FIG. 2, the PDA device 200 includes an operation input unit 201, a processing-and-control unit 202, a wireless communicating unit 205, which includes the wireless reception unit 203 and a wireless transmission unit 204, a power supply unit 206, a display unit 207, and a contact sensor 208.

For example, when an examiner has performed an input operation on the PDA device 200, the operation input unit 201 inputs input-operation information based on the input operation to the processing-and-control unit 202.

The processing-and-control unit 202 integrally controls, on the basis of the input-operation information input from the operation input unit 201, a reception signal received by the wireless reception unit 203, a sensing signal from the contact sensor 208 and the like, various processing and operations to be performed in the PDA device 200.

The wireless communicating unit 205 wirelessly communicates with the ophthalmic apparatus 100 on the basis of a control signal from the processing-and-control unit 202 and includes the wireless reception unit 203 and the wireless transmission unit 204 as illustrated in FIG. 2.

For example, the wireless reception unit 203 receives the above-mentioned moving-image signals and the above-mentioned eye-examination control signal from the ophthalmic apparatus 100. In addition, for example, the wireless reception unit 203 receives the identification information that is used to identify the ophthalmic apparatus 100 from the ophthalmic apparatus 100. The wireless reception unit 203 is equipped with a circuit that detects the intensity of an electric field in wireless communication and a transmission/reception delay time in wireless communication so that the wireless reception unit 203 can detect the distance between the PDA device 200 and the ophthalmic apparatus 100. Although, in the present embodiment, the circuit, which detects the intensity of an electric field in wireless communication and a transmission/reception delay time in wireless communication, is built into the wireless reception unit 203 of the PDA device 200, for example, a configuration in which the circuit is built into the wireless reception unit 113 of the ophthalmic apparatus 100 may be employed.

For example, the wireless transmission unit 204 transmits, to the ophthalmic apparatus 100, a setting information item related to an examination (an eye examination) that is to be performed by the eye-examination unit 101, a number-of-times information item related to the eye examination, an information item regarding an alignment operation performed by the eye-examination unit 101, an information item regarding an eye-examination starting operation related to the eye examination, and the like. Note that, in the present invention, the wireless transmission unit 204 may be configured to transmit at least one information item of these information items.

The power supply unit 206 supplies power to the processing-and-control unit 202, the wireless reception unit 203, the wireless transmission unit 204, the display unit 207, and the contact sensor 208.

The display unit 207 displays a screen containing various images and various information items on the basis of a control signal from the processing-and-control unit 202. For example, the display unit 207 displays, under control of the processing-and-control unit 202, a screen containing a moving image based on moving-image signals of a target eye, which have been transmitted by the ophthalmic apparatus 100, and an eye-examination control information item based on an eye-examination control signal, which has been transmitted by the ophthalmic apparatus 100.

The contact sensor 208 is a sensing unit that detects contact between the PDA device 200 and the ophthalmic apparatus 100.

A control method used by the processing-and-control unit 202 of the PDA device 200 according to the present embodiment will now be described below.

The processing-and-control unit 202 performs display control for switching a screen to be displayed by the display unit 207 in accordance with the positional relationship between the processing-and-control unit 202 and the ophthalmic apparatus 100. The processing-and-control unit 202, which performs the display control, serves as a display control unit.

For example, first, the processing-and-control unit 202 performs detection processing for detecting the ophthalmic apparatus 100 in the following cases: the case where the contact sensor 208 has detected contact between the ophthalmic apparatus 100 and the PDA device 200 and the case where the ophthalmic apparatus 100 is not in contact with the PDA device 200 and where the distance between the ophthalmic apparatus 100 and the PDA device 200 is smaller than a predetermined distance (e.g., the case where the processing-and-control unit 202 has detected that near field communication had been performed between the wireless communicating unit 205 and the ophthalmic apparatus 100 or the case where the circuit, which is included in the wireless reception unit 203 (or the wireless reception unit 113) and which detects the distance between the ophthalmic apparatus 100 and the PDA device 200, has detected a distance smaller than a predetermined distance). The processing-and-control unit 202, which performs the detection processing, serves as a detection unit. After the processing-and-control unit 202 has detected the ophthalmic apparatus 100, the processing-and-control unit 202 performs display control so as to cause the display unit 207 to display a screen related to the ophthalmic apparatus 100. In this case, the processing-and-control unit 202 causes the display unit 207 to display a screen that contains a moving image based on the above-mentioned moving-image signals, which have been obtained by the ophthalmic apparatus 100, and an eye-examination control information item based on the above-mentioned eye-examination control signal, which has been obtained by the ophthalmic apparatus 100.

According to the above configuration, in the case where the ophthalmic apparatus 100 is not detected (e.g., the case where an eye examination is not performed by using the ophthalmic apparatus 100), information regarding patients awaiting examinations, patient information regarding a patient who will undergo an eye examination next, and the like can be displayed by the display unit 207 of the PDA device 200, and in the case where the ophthalmic apparatus 100 has been detected as a result of the PDA device 200 being brought close to the ophthalmic apparatus 100 by an examiner (e.g., the case where an eye examination is performed by using the ophthalmic apparatus 100), the screen displayed by the display unit 207 can be switched to a screen related to the ophthalmic apparatus 100. Therefore, an eye examination can be performed with good efficiency.

In the case where the ophthalmic system 10 includes a plurality of ophthalmic apparatuses 100 each of which is capable of communicating with (capable of wirelessly communicating with) the PDA device 200, the processing-and-control unit 202 can perform the following processing.

For example, first, the processing-and-control unit 202 performs detection processing for detecting one of the plurality of ophthalmic apparatuses 100, the ophthalmic apparatus 100 being located closer to the PDA device 200 than other ophthalmic apparatuses. As an example of this, the processing-and-control unit 202 performs detection processing for detecting one of the plurality of ophthalmic apparatuses 100, the ophthalmic apparatus 100 being located closest to the PDA device 200. In this case, the processing-and-control unit 202 performs detection processing for detecting the ophthalmic apparatus 100 that has been brought into contact with the PDA device 200 or the ophthalmic apparatus 100 that is not in contact with the PDA device 200 but is spaced to be closer than the other ophthalmic apparatuses 100 to the PDA device 200. The processing-and-control unit 202, which performs the detection processing, serves as a detection unit. Next, the processing-and-control unit 202 performs display control for causing the display unit 207 to display a screen related to the ophthalmic apparatus 100, which has been detected. More specifically, the processing-and-control unit 202 causes the display unit 207 to display a screen that contains a moving image based on the above-mentioned moving-image signals obtained by the detected ophthalmic apparatus 100 and an eye-examination control information item based on the above-mentioned eye-examination control signal obtained by the detected ophthalmic apparatus 100. According to this configuration, information regarding the ophthalmic apparatus 100 that is actually used for performing an eye examination among the plurality of ophthalmic apparatuses 100 can be displayed by the display unit 207 of the PDA device 200, and consequently, an eye examination can be performed with good efficiency.

A screen that is to be displayed by the display unit 207 of the PDA device 200 will now be described.

FIG. 4 to FIG. 7B are diagrams each illustrating an example of the appearance of the PDA device 200 according to the embodiment of the present invention. The same components in FIG. 4 to FIG. 7B are denoted by the same reference numerals. For example, one of apparatuses called tablet personal computers (PC), smartphones, and notebook-sized PCs may be employed as the PDA device 200 according to the present embodiment. In this case, in the PDA device 200, a touch-panel operation can be performed on a relatively large screen, and in addition, a plurality of windows can be displayed. A touch panel in this case serves as the operation input unit 201 illustrated in FIG. 2.

Figure 4:
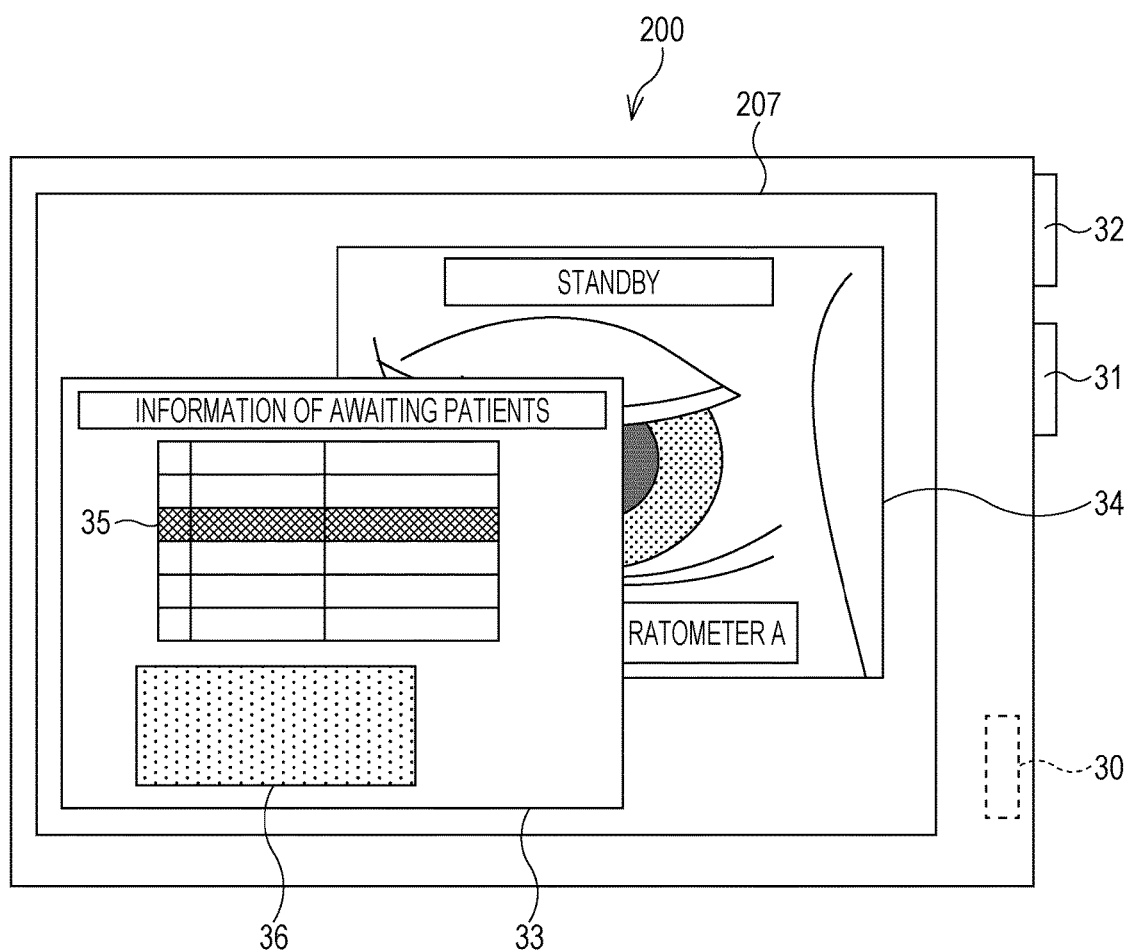
FIG. 4 is a diagram illustrating an example of the appearance of the personal digital assistant device according to the embodiment of the present invention.

As illustrated in FIG. 4, a wireless LAN communication device 30 capable of performing wireless communication is built into the PDA device 200. In addition, as illustrated in FIG. 4, the PDA device 200 is provided with an external communication device 31 that is compatible with Bluetooth (Registered Trademark) and that is to be connected to a universal serial bus (USB) connector and with an external near field communication device 32 that is to be connected to a USB connector. In the example illustrated in FIG. 4, although the communication device 31 is an external communication device that is compatible with Bluetooth (Registered Trademark) and that is to be connected to a USB connector, a configuration in which the communication device 31 is built into the PDA device 200 may be employed. The wireless LAN communication device 30, the communication device 31 that is compatible with Bluetooth (Registered Trademark), and the near field communication device 32 each serve as the wireless communicating unit 205 illustrated in FIG. 2.

When an examiner holds the PDA device 200 and is located at a position spaced apart from the ophthalmic apparatus 100, a window 33 showing statuses of awaiting patients and a window 34 regarding the ophthalmic apparatus 100 that is performing wireless video communication and that is in an observation state are displayed by the display unit 207 illustrated in FIG. 4. In the window 33, a patient who is undergoing an eye examination is highlighted and displayed (highlighting display 35), and information regarding the patient is displayed in a comment column 36. The screen showing the statuses of awaiting patients is an exemplary embodiment forming a component of an application in a local network of a hospital or a system for use in ophthalmic diagnosis.

Figure 5:
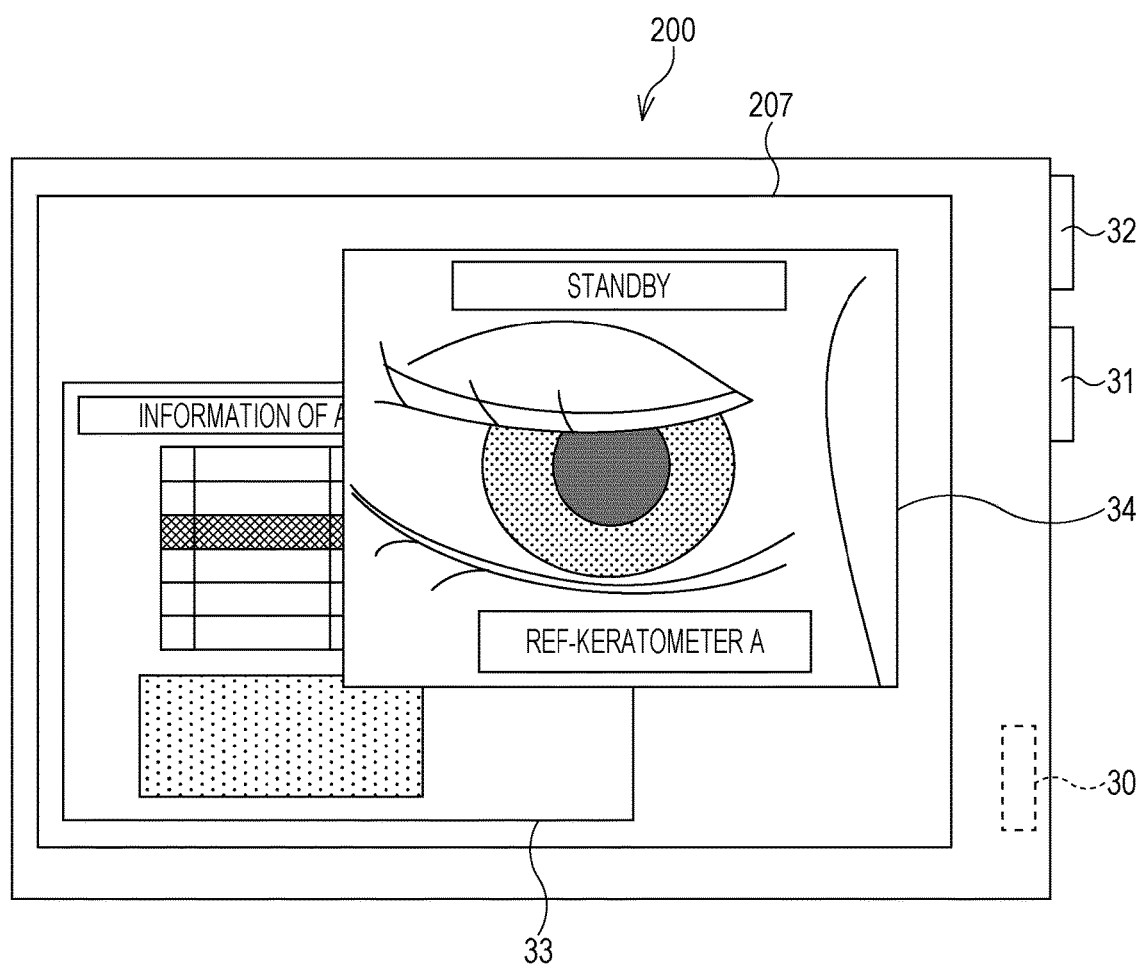
FIG. 5 is a diagram illustrating an example of the appearance of the personal digital assistant device according to the embodiment of the present invention.

An examiner touches the window 34 illustrated in FIG. 4, and as a result, the window 34, which displays an observation state of the image-capturing unit 109 of the ophthalmic apparatus 100, comes to the front as illustrated in FIG. 5. Here, high-speed wireless communication is performed so that the state of a target eye can be observed as described above even at a position spaced apart from the ophthalmic apparatus 100. Next, assume that the examiner comes close to the ophthalmic apparatus 100 while holding the PDA device 200 or assume that the examiner places the PDA device 200 on the rack 107 of the ophthalmic apparatus 100.

Figure 6:
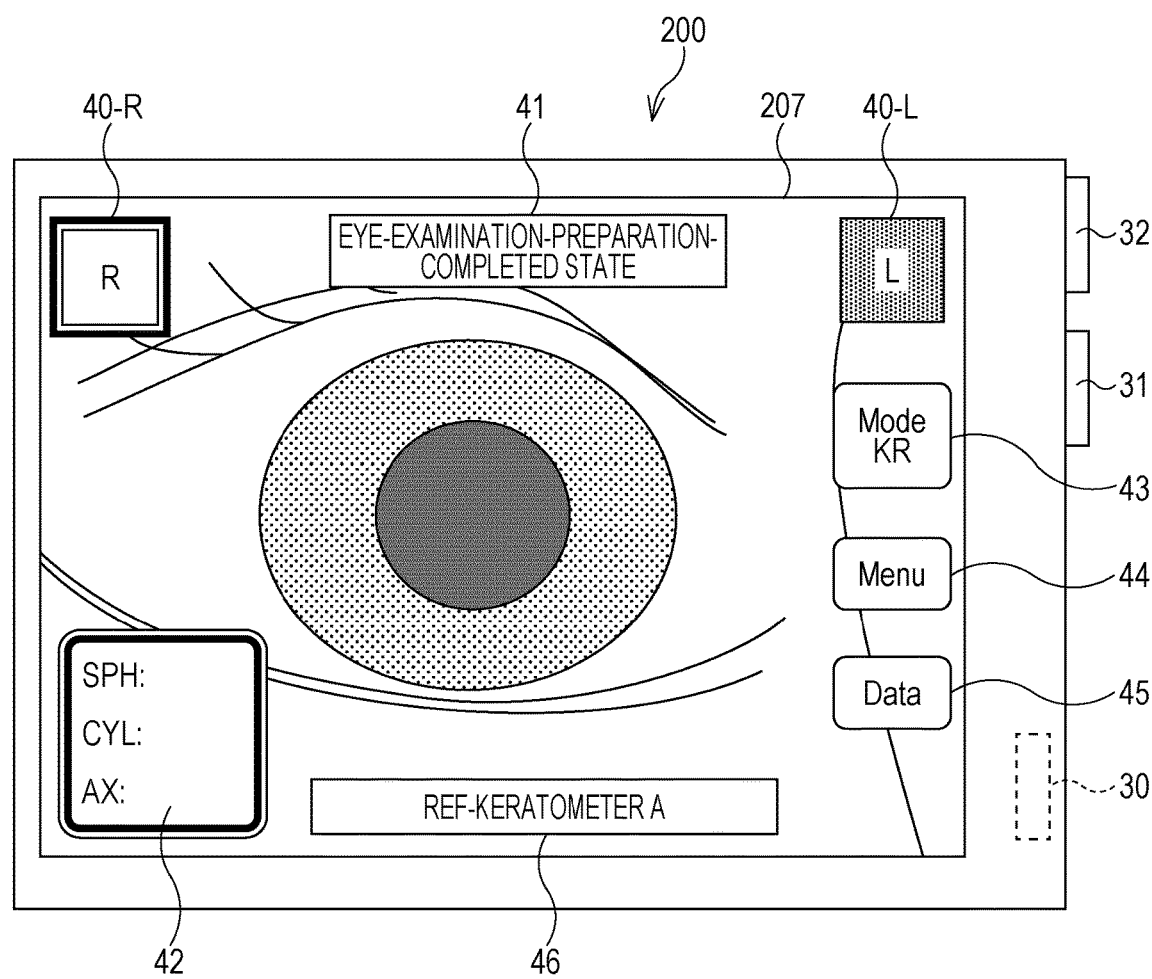
FIG. 6 is a diagram illustrating an example of the appearance of the personal digital assistant device according to the embodiment of the present invention.

In this case, the wireless reception unit 203 of the PDA device 200 receives, from the wireless transmission unit 114 of the ophthalmic apparatus 100, a control signal indicating that the PDA device 200 has been brought close to the ophthalmic apparatus 100 and sends a response to the control signal back to the wireless reception unit 113, and as a result, the screen of the display unit 207 is switched to a screen such as that illustrated in FIG. 6 showing an eye-examination-preparation-completed state.

In FIG. 6, screens 40-R and 40-L are each a screen indicating which one of left and right eyes is to be examined, and a position sensor incorporated in a left-right moving mechanism within the ophthalmic apparatus 100 determines which one of the left and right eyes is in an examinable state. The example illustrated in FIG. 6 shows that the right eye (screen 40-R) is in an examinable state.

In FIG. 6, a screen 41 is a status screen and displays "eye-examination-preparation-completed state" when preparation for an eye examination has been completed and displays "undergoing eye examination" or "undergoing measurement" when an eye examination is being performed. In the case where a measurement has been successfully completed, the screen 41 displays "eye examination successfully completed" or the like. In addition, in the case where some errors have occurred, the screen 41 can highlight and display an error message. As a result of touching the screen 41 displaying the "eye-examination-preparation-completed state", a control signal for starting an operation is transmitted to the ophthalmic apparatus 100, and the control signal acts as a trigger for enabling an alignment operation and eye-examination settings (described later).

In FIG. 6, a screen 42 displays measurement results obtained immediately after performing an eye examination. Since the state illustrated in FIG. 6 is before an eye examination is performed, the screen 42 is left blank. When a measurement has been successfully completed, the screen 42 displays the measurement results, and when an error has occurred in the measurement, the screen 42 displays the error. On the screen 42, "SPH", "CYL", and "AX" respectively represent the spherical power of a target eye, the cylindrical power of the target eye, and the axial angle of the target eye.

In FIG. 6, a screen 43 is a screen and a button used for switching an eye-examination mode, and by touching the screen 43, the eye-examination mode can be switched from a mode in which kerato measurement and ref measurement are performed to other modes such as a mode in which only kerato measurement is performed and a mode in which only ref measurement is performed.

In FIG. 6, a screen 44 also serves as a button used for changing the settings of the ophthalmic apparatus 100. Pressing this button enables lower layer settings, and accordingly, various settings for the ophthalmic apparatus 100 can be performed.

In FIG. 6, a screen 45 also serves as a button that enables a screen to transition to a screen used for checking the details of measurement results.

In FIG. 6, a screen 46 displays the name of the ophthalmic apparatus 100 based on identification information transmitted by the ophthalmic apparatus 100. An examiner can change the name displayed on the screen 46 to a desired name on a setting screen, so that in the case of operating a plurality of ophthalmic apparatuses, which will be described later, the plurality of ophthalmic apparatuses can be identified.

Through button operations such as those described above, the eye-examination-unit controller 111 is controlled by an electrical signal transmitted from the wireless control unit 112 via the wireless reception unit 113 of the ophthalmic apparatus 100, so that changes in the eye-examination unit 101 according to the eye-examination mode can be made, and switching of various settings of the ophthalmic apparatus 100 according to the eye-examination mode can be performed.

Figure 7A:
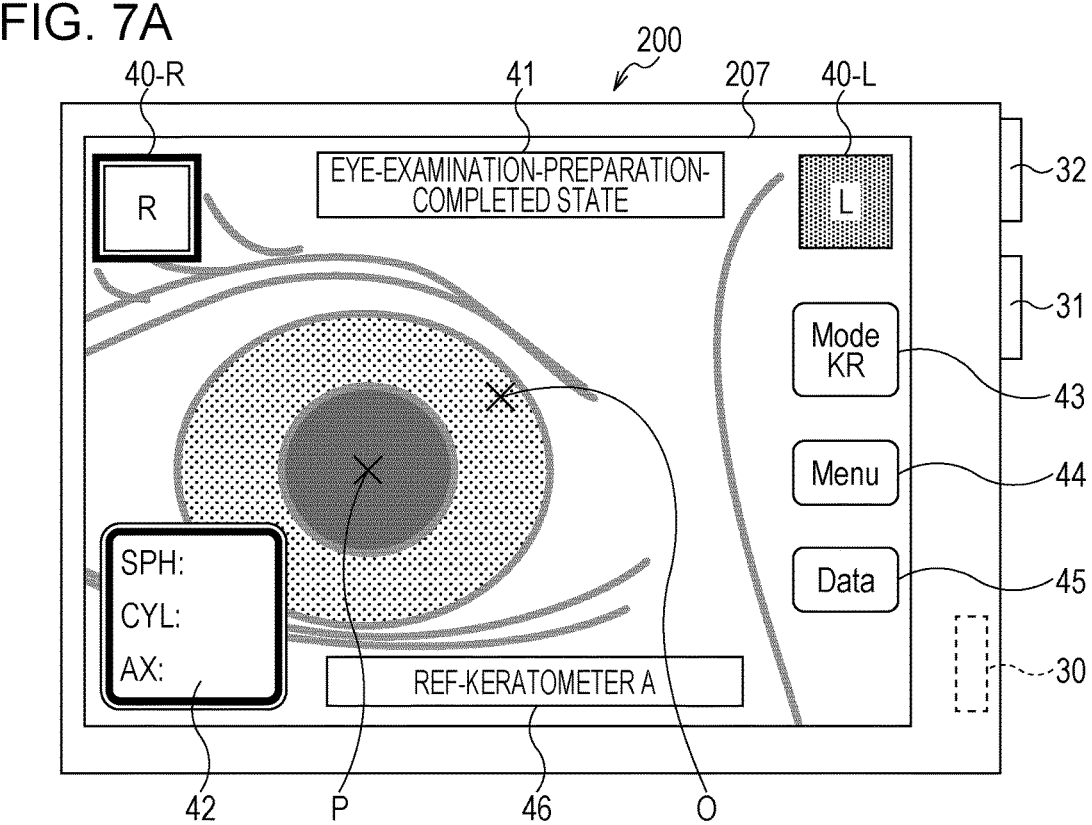
FIGS. 7A and 7B are diagrams each illustrating an example of the appearance of the personal digital assistant device according to the embodiment of the present invention.

FIG. 7A illustrates a screen displaying a state where the alignment of a target eye is offset toward the lower left side and where the position of the target eye in a front-rear direction is also offset. When an examiner moves their finger in a direction toward a point O while touching a point P illustrated in FIG. 7A by the finger, a control signal of an alignment instruction is transmitted from the PDA device 200 to the ophthalmic apparatus 100 by wireless communication. Then, in the ophthalmic apparatus 100, the eye-examination-unit controller 111 drives the vertical driving unit 102 and the left-right-and-front-rear driving unit 103 on the basis of the control signal and causes the eye-examination unit 101 to move in accordance with the operation performed by the examiner.

Regarding the position of the ophthalmic apparatus 100 with respect to a target eye in the front-rear direction, for example, the ophthalmic apparatus 100 can be moved in a backward direction by making a pinching gesture using two fingers positioned at two points on the screen, and the ophthalmic apparatus 100 can be moved in a forward direction by making a stretching gesture using two fingers positioned at two points on the screen. In the case where the ophthalmic apparatus 100 has an auto alignment function of projecting an alignment index light onto a target eye and detecting the position of reflected light, which is the alignment index light that has been reflected, by using a position sensor (not illustrated), the ophthalmic apparatus 100 is automatically positioned as a result of positioning the alignment index light within a predetermined area, and a moving-image signal related to this operation can be transmitted to the PDA device 200 via the wireless transmission unit 114.

Figure 7B:
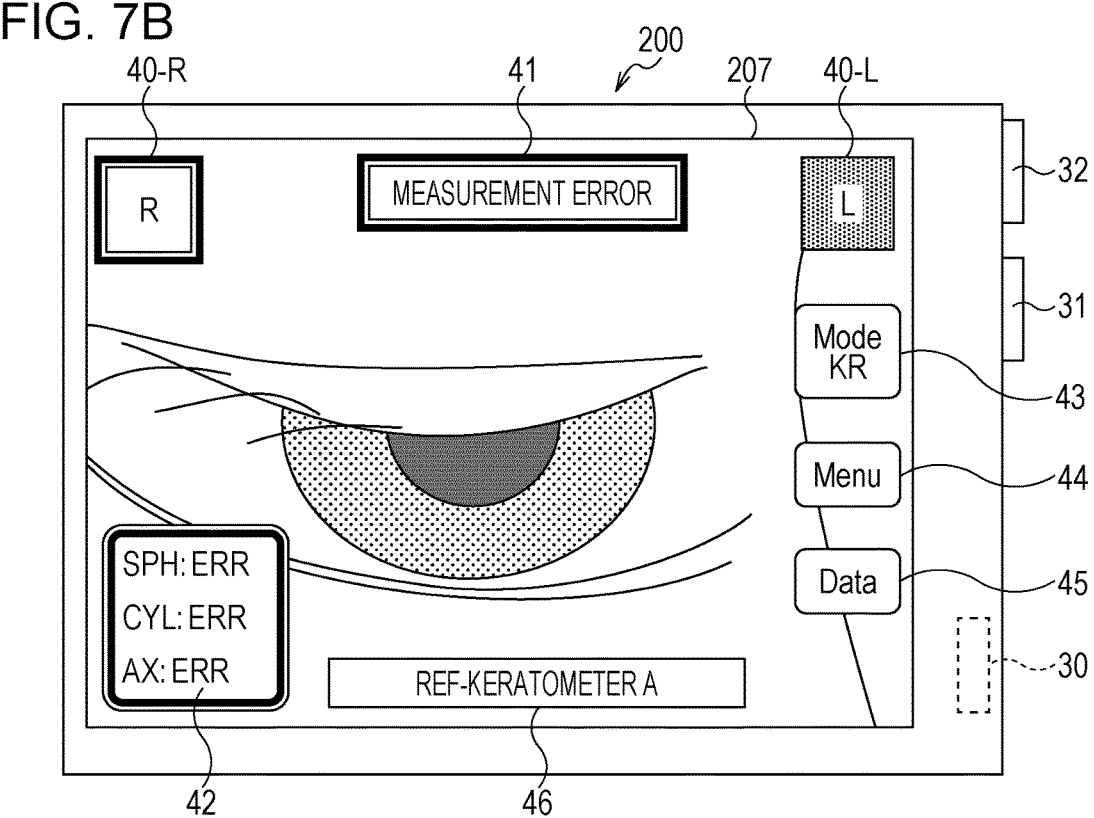

FIG. 7B illustrates a screen displaying a still image in the case where a measurement error has occurred. An examiner may show a patient this screen by pointing the PDA device 200 toward the patient, so that the examiner can tell the patient why the measurement error has occurred. FIG. 7B illustrates the case where the eyelid opening state of a target eye is insufficient, and in this case, an examiner can give an instruction to prompt the patient to open their eyes wider.

A process in a control method used in the ophthalmic system 10 according to the embodiment of the present invention will now be described.

FIG. 8 is a flowchart illustrating an exemplary process in a control method used in the ophthalmic system 10 according to the embodiment of the present invention. The process illustrated in FIG. 8 will be described with reference to the configurations of the units illustrated in FIG. 2.

FIG. 8 illustrates the PDA device 200, an ophthalmic apparatus A (100-A) that is to be detected, and a moving-image signal 51 and an eye-examination control signal 52, each of which is transmitted and received between the PDA device 200 and the ophthalmic apparatus A (100-A).

When the power supply unit 104 of the ophthalmic apparatus A (100-A) has been switched on in a state where the PDA device 200 is in an enabled state, for example, the wireless control unit 112 of the ophthalmic apparatus A (100-A) detects that the power supply unit 104 has been switched on in step ST101. Then, the wireless control unit 112 of the ophthalmic apparatus A (100-A) transmits, to the PDA device 200 via the wireless transmission unit 114, a state-confirmation signal S1-1 indicating that the preparations for an eye examination has been completed.

After the PDA device 200 has received the state-confirmation signal S1-1, the processing-and-control unit 202 detects the ophthalmic apparatus A (100-A) in step ST102. Then, the processing-and-control unit 202 causes the display unit 207 to display the window 34 illustrated in FIG. 4. After the ophthalmic apparatus A (100-A) has been detected, the PDA device 200 opens the window 34 and transmits a state-confirmation signal S1-2 indicating that the preparations for a procedure has been completed to the ophthalmic apparatus A (100-A) via the wireless transmission unit 204.

After the ophthalmic apparatus A (100-A) has received the state-confirmation signal S1-2, the eye-examination-unit controller 111 causes the eye-examination unit 101 to start observing a target eye in step ST103. More specifically, in the present embodiment, the wireless reception unit 113 receives the state-confirmation signal S1-2 from the PDA device 200 in the following cases: the case where the ophthalmic apparatus A (100-A) has been brought into contact with the PDA device 200 and the case where the ophthalmic apparatus A (100-A) is not in contact with the PDA device 200 and where the distance between the ophthalmic apparatus A (100-A) and the PDA device 200 is smaller than a predetermined distance. Then, an observation image captured by the eye-examination unit 101 is transmitted to the PDA device 200 as an observation moving image signal S2 in the above-mentioned moving-image signal 51 in high-speed wireless communication.

Although, as illustrated in FIG. 5, a moving image based on the observation moving image signal S2 can be viewed by using the PDA device 200, the status of the ophthalmic apparatus A (100-A) is a standby state. When an examiner brings the PDA device 200 close to the ophthalmic apparatus A (100-A) or places the PDA device 200 on the ophthalmic apparatus A (100-A), the processing-and-control unit 202 performs display control so as to cause the display unit 207 to switch the screen displayed by the display unit 207 to a screen such as that illustrated in FIG. 6 showing an eye-examination-preparation-completed state.

After the examiner has performed an eye-examination setting operation by touching the screen displayed by the display unit 207, the processing-and-control unit 202 detects that the eye-examination setting operation has been performed in step ST104. Subsequently, the processing-and-control unit 202 transmits a setting signal S3 based on the eye-examination setting operation to the ophthalmic apparatus A (100-A) via the wireless transmission unit 204.

After the ophthalmic apparatus A (100-A) has received the setting signal S3, the eye-examination-unit controller 111 performs, on the eye-examination unit 101 in step ST105, an eye-examination setting operation based on the setting signal S3. In other words, the eye-examination settings of the eye-examination unit 101 are changed to eye-examination settings based on the setting signal S3.

In step ST106, the processing-and-control unit 202 performs control so as to cause the display unit 207 to display, for example, a screen such as that illustrated in FIG. 7A showing an eye-examination-preparation-completed state. Then, the examiner performs an alignment operation such as that illustrated in FIG. 7A, after which the processing-and-control unit 202 detects that the alignment operation has been performed in step ST107. Subsequently, the processing-and-control unit 202 transmits an operation signal S4 based on the alignment operation to the ophthalmic apparatus A (100-A) via the wireless transmission unit 204.

After the ophthalmic apparatus A (100-A) has received the operation signal S4, the eye-examination-unit controller 111 drives the vertical driving unit 102 and the left-right-and-front-rear driving unit 103 and positions the eye-examination unit 101 with respect to the target eye in step ST108. In this case, the moving-image signal is transmitted as an observation moving image signal S5 to the PDA device 200.

After the PDA device 200 has received the observation moving image signal S5, the processing-and-control unit 202 performs control so as to cause the display unit 207 to display a moving image based on the observation moving image signal S5. After that, the examiner touches the screen of the display unit 207 and performs an eye-examination starting operation, and then, the processing-and-control unit 202 detects that the eye-examination starting operation has been performed in step ST109. Subsequently, the processing-and-control unit 202 transmits an operation signal S6 based on the eye-examination starting operation to the ophthalmic apparatus A (100-A) via the wireless transmission unit 204.

After the ophthalmic apparatus A (100-A) has received the operation signal S6, the eye-examination-unit controller 111 causes the eye-examination unit 101 to perform examination of the target eye in step ST110. After that, the eye-examination-unit controller 111 transmits an eye-examination-result signal S7 related to the results of the examination of the target eye, which has been performed by the eye-examination unit 101, to the PDA device 200 via the wireless control unit 112 and the wireless transmission unit 114. In other words, in the ophthalmic apparatus A (100-A), after the observation moving image signal S5 has been transmitted to the PDA device 200, the wireless reception unit 113 receives the operation signal S6 (or the operation signal S4) from the PDA device 200, and the wireless transmission unit 114 transmits, to the PDA device 200 on the basis of the operation signal received by the wireless reception unit 113, the eye-examination-result signal S7 representing the examination results of the target eye. Regarding the eye-examination-result signal S7, in the case where the ophthalmic apparatus A (100-A) is a tonometer, the examination results of the target eye include the values of intraocular pressure, corneal thickness, and the like, and in the case where the ophthalmic apparatus A (100-A) is an auto ref-keratometer, the examination results of the target eye include the refractive value, the degree of astigmatism, the axial angle, the radius of corneal curvature, and the like. In addition, regarding the eye-examination-result signal S7, in the case where the ophthalmic apparatus A (100-A) is a fundus camera, the examination results of the target eye include a still image of an eye fundus and the like. In the present embodiment, the eye-examination-result signal S7 includes an image showing corneal thickness and a ring image showing a refractive value, which have been used in the measurement, and an error image showing an error that has occurred as well as the examination results of the target eye.

After the PDA device 200 has received the eye-examination-result signal S7, the processing-and-control unit 202 causes, in step ST111 and step ST112, the display unit 207 to display the eye examination results (ST111) based on the eye-examination-result signal S7 or an eye examination error (ST112) based on the eye-examination-result signal S7.

After that, in step ST113, the processing-and-control unit 202 brings the PDA device 200 into a standby state. In this standby state, an examination of a target eye has been completed, and the display unit 207 of the PDA device 200 displays the window 34 illustrated in FIG. 5 again. Subsequently, the processing-and-control unit 202 transmits a state-confirmation signal S8 based on the standby state to the ophthalmic apparatus A (100-A) via the wireless transmission unit 204.

After the ophthalmic apparatus A (100-A) has received the state-confirmation signal S8, the eye-examination-unit controller 111 switches off the light source of the eye-examination unit 101, which has been in a ready-to-measure state, or reduces the intensity of the light source and brings the ophthalmic apparatus A (100-A) into the standby state in step ST114. Then, the eye-examination-unit controller 111 continuously transmits, to the PDA device 200 via the wireless control unit 112 and the wireless transmission unit 114, an observation moving image signal S9 based on an observation moving image that has been obtained, in the standby state, by the image-capturing unit 109 via the observation optical system 108, which is built into in the eye-examination unit 101. In this manner, in the standby state, an observation moving image based on the observation moving image signal S9 can be constantly displayed by the display unit 207 in the PDA device 200.

According to the process illustrated in FIG. 8, as a result of the moving-image signal 51 and the examination control signal 52 being transmitted and received between the PDA device 200 and the ophthalmic apparatus A (100-A) by wireless communication, an examiner can check patient information regarding the next patient, effectively perform an eye-examination operation, and show an error screen to a patient. Accordingly, an eye examination can be performed with good efficiency.

A common personal digital assistant device can display a plurality of window screens and is configured to display information other than information regarding an eye examination, and thus, when an examiner actually performs an eye examination, the examiner needs to perform complicated operations including operations for searching for and displaying a window screen used for the eye examination. On the other hand, in the PDA device 200 according to the present embodiment, a screen to be displayed by the display unit 207 is switched in accordance with the positional relationship between the PDA device 200 and the ophthalmic apparatus 100, and thus, it is not necessary to perform complicated operations for searching for and displaying a window screen used for an eye examination.

Although the ophthalmic apparatus A (100-A) is the only one ophthalmic apparatus that wirelessly communicates with the PDA device 200 in the example illustrated in FIG. 8, the present invention is not limited to this embodiment. For example, in a hospital in which a plurality of ref-keratometers, each of which is an ophthalmic apparatus, are installed, the plurality of ref-keratometers can be operated by using one PDA device 200. In the case where there are three ref-keratometers, which are a ref-keratometer A (100-A), a ref-keratometer B (100-B), and a ref-keratometer C (100-C), unique identification information items IDa, IDb, and IDc are respectively given to the ref-keratometer A (100-A), the ref-keratometer B (100-B), and the ref-keratometer C (100-C) so that each of the ref-keratometers can be identified. For example, when the ref-keratometer A (100-A) has been switched on, the identification information item IDa is caused to be included in the state-confirmation signal S1-1 illustrated in FIG. 8, and the state-confirmation signal S1-1 is transmitted to the PDA device 200. Then, a window for the ref-keratometer A appears. Similarly, when the ref-keratometer B (100-B) and the ref-keratometer C (100-C) have been switched on, windows corresponding to the ref-keratometer B (100-B) and the ref-keratometer C (100-C) appear. Accordingly, a plurality of ophthalmic apparatuses 100 can be operated by using one PDA device 200. In addition, other different types of ophthalmic apparatuses, such as a tonometer and a fundus camera, can be added as additional ophthalmic apparatuses to be operated by switching them on.

The ophthalmic system 10 according to the present embodiment may have the following configuration.

In the case where the PDA device 200 has detected the ophthalmic apparatus A (100-A), when the distance between the PDA device 200 and the detected ophthalmic apparatus A (100-A) is equal to or greater than a predetermined distance as a result of an examiner moving while holding the PDA device 200, and a certain time has passed, the PDA device 200 and the ophthalmic apparatus A (100-A) perform the following processing.

In this case, in the PDA device 200, the processing-and-control unit 202 performs display control so as to cause the display unit 207 to display an icon used for selecting whether to disconnect the communication between the PDA device 200 and the detected ophthalmic apparatus A (100-A) or not. Then, in the PDA device 200, when the examiner has selected to disconnect the communication between the PDA device 200 and the ophthalmic apparatus A (100-A), the wireless transmission unit 204 transmits, under control of the processing-and-control unit 202, a communication-disconnection signal to the ophthalmic apparatus A (100-A).

In this case, in the ophthalmic apparatus A (100-A), the wireless reception unit 113 receives the communication-disconnection signal from the PDA device 200. Then, in the ophthalmic apparatus A (100-A), the wireless control unit 112 performs, on the basis of the communication-disconnection signal received by the wireless reception unit 113, communication-disconnection processing for disconnecting the communication between the PDA device 200 and the ophthalmic apparatus A (100-A). The wireless control unit 112, which performs the communication-disconnection processing, serves as a communication-disconnection unit.

Alternatively, the ophthalmic system 10 according to the present embodiment may have the following configuration.

As described above, in the case where a plurality of ophthalmic apparatuses 100 are configured to be capable of communicating with the PDA device 200, the PDA device 200 performs the following processing.

In the PDA device 200, in the case where the plurality of ophthalmic apparatuses 100 have been detected, the processing-and-control unit 202 performs display control so as to cause the display unit 207 to display a selection screen used for selecting one of the plurality of ophthalmic apparatuses 100. In the PDA device 200, after one of the ophthalmic apparatuses 100 has been selected by an examiner, the processing-and-control unit 202 performs display control so as to cause the display unit 207 to display a screen related to the selected ophthalmic apparatus 100.

Alternatively, the ophthalmic system 10 according to the present embodiment may have the following configuration.

More specifically, when the ophthalmic apparatus A (100-A) that has been detected by the PDA device 200 is already being used, the wireless transmission unit 114 transmits information indicating that the ophthalmic apparatus A (100-A) is already being used to the PDA device 200.

In this case, in the PDA device 200, the wireless reception unit 203 receives the information indicating that the ophthalmic apparatus A (100-A), which has been detected, is already being used from the ophthalmic apparatus A (100-A). Then, in the PDA device 200, the processing-and-control unit 202 performs, on the basis of the information received by the wireless reception unit 203, display control so as to cause the display unit 207 to display information indicating that the ophthalmic apparatus A (100-A), which has been detected, is already being used.

Alternatively, the ophthalmic system 10 according to the present embodiment may have the following configuration.

Before the ophthalmic apparatus A (100-A) is detected by the PDA device 200, in the PDA device 200, the processing-and-control unit 202 causes the display unit 207 to display a screen regarding awaiting patients. After the ophthalmic apparatus A (100-A) has been detected, in the PDA device 200, the processing-and-control unit 202 performs display control so as to switch the screen displayed by the display unit 207 from the screen regarding awaiting patients to a screen related to the ophthalmic apparatus A (100-A).

According to the ophthalmic system 10 of the present embodiment, even in the case where the PDA device 200 is configured to be capable of communicating with a plurality of ophthalmic apparatuses 100, switching between screens each of which is appropriate for a corresponding one of the ophthalmic apparatuses 100 can be performed, and accordingly, an eye examination can be performed with good efficiency. In addition, an operation screen of an ophthalmic apparatus that is desired to be used by an examiner in an eye examination can be automatically displayed without requiring the examiner to search for the operation screen, and thus, the efficiency of operations to be performed by the examiner can be improved.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-102838, filed May 20, 2015, which is hereby incorporated by reference herein in its entirety.

What is claimed is:

1. An ophthalmic apparatus that is capable of communicating with a personal digital assistant (PDA) device, the PDA device including a display unit, the ophthalmic apparatus comprising:

a main body that includes an image-capturing unit, the image-capturing unit obtaining a moving image of an eye to be examined using light returned from the eye to be examined which is illuminated, the main body being for obtaining information regarding the eye to be examined;

a driving unit that drives the main body;

a transmission unit that transmits, before the information regarding the eye to be examined is obtained, a moving image signal of the obtained moving image, to the PDA device;

a reception unit that receives a control signal from the PDA device when the moving image signal is transmitted; and a control unit that controls the driving unit using the received control signal.

2. The ophthalmic apparatus according to claim 1, wherein the reception unit receives, from the PDA device, a signal of an instruction issued on the moving image which is displayed on the display unit based on the moving image signal received by the PDA device, as the control signal.

3. The ophthalmic apparatus according to claim 1, further comprising:

a sensing unit that detects that a distance between the main body and the PDA device is smaller than a predetermined distance by wireless communication, wherein the transmission unit transmits the moving image signal to the PDA device when it is determined that the distance is smaller than the predetermined distance.

4. The ophthalmic apparatus according to claim 1, further comprising:

a sensing unit that detects that the distance between the main body and the PDA device is smaller than a predetermined distance as a result of the main body and the PDA device making contact with each other, wherein the transmission unit transmits the moving image signal to the PDA device when it is determined that the distance is smaller than the predetermined distance.

5. An ophthalmic apparatus that is capable of communicating with a personal digital assistant (PDA) device, the ophthalmic apparatus comprising:

an eye-examination unit that performs an examination on an eye to be examined;

a reception unit that receives a state-confirmation signal from the PDA device when the ophthalmic apparatus is brought into contact with the PDA device or when the ophthalmic apparatus is not in contact with the PDA device, and a distance between the ophthalmic apparatus and the PDA device is smaller than a predetermined distance; and a transmission unit that transmits, to the PDA device, a moving image signal of the eye to be examined obtained before performing the examination.

6. The ophthalmic apparatus according to claim 5, wherein the reception unit further receives an operation signal from the PDA device after the moving image signal has been transmitted to the PDA device, and wherein the transmission unit further transmits, based on the received operation signal, an eye-examination-result signal representing results of the examination performed on the eye to be examined to the PDA device.

7. The ophthalmic apparatus according to claim 5, wherein the transmission unit transmits the moving image signal to the PDA device by using Bluetooth or a high-speed wireless local area network (LAN) communication standard.

8. The ophthalmic apparatus according to claim 5,
wherein the transmission unit further transmits, to the PDA device by using a near field communication standard that uses a frequency band of 13.56 MHz, an eye-examination control signal that includes at least one of a set-value information item related to the examination, an eye-examination-mode-state information item related to the examination, an information item regarding left and right eyes each of which is the eye to be examined, an information item regarding a presence or absence of an eye-examination error related to the examination, and an eye-examination-result information item based on the eye-examination-result signal representing results of the examination.

9. The ophthalmic apparatus according to claim 5,
wherein the transmission unit further transmits identification information that is used to identify the ophthalmic apparatus to the PDA device.

10. The ophthalmic apparatus according to claim 5,
wherein the reception unit further receives, from the PDA device, at least one of a setting information item related to the examination, a number-of-times information item related to the examination, an information item regarding an alignment operation performed by the eye-examination unit, and an information item regarding an eye-examination starting operation related to the examination.

11. The ophthalmic apparatus according to claim 5,
wherein the reception unit further receives a communication-disconnection signal from the PDA device when the distance between the ophthalmic apparatus and the PDA device is not less than a predetermined distance, and a certain time has passed, and
wherein the ophthalmic apparatus further comprises a communication-disconnection unit that disconnects communication between the ophthalmic apparatus and the PDA device based on the received communication-disconnection signal.

12. The ophthalmic apparatus according to claim 5,
wherein, when the ophthalmic apparatus is already being used, the transmission unit further transmits information indicating that the ophthalmic apparatus is already being used to the PDA device.

13. A personal digital assistant (PDA) device that is capable of communicating with an ophthalmic apparatus comprising a main body for obtaining information regarding an eye to be examined and that includes a display unit, the PDA device comprising:
a reception unit that receives, from the ophthalmic apparatus, a moving image signal indicating a moving image of the eye to be examined, before the information regarding the eye to be examined is obtained, the moving image being obtained by an image-capturing unit using light returned from the eye to be examined which is illuminated;
a display control unit that causes the display unit to display the moving image; and
a transmission unit that transmits, when the moving image signal is received, a control signal to the ophthalmic apparatus using information about an instruction issued on the displayed moving image.

14. The PDA device according to claim 13,
wherein the PDA device comprises at least one of a tablet personal computer, a smartphone, and a notebook-sized personal computer.

15. A personal digital assistant (PDA) device that is capable of communicating with at least one ophthalmic apparatus, wherein the at least one ophthalmic apparatus performs an examination on an eye to be examined, the PDA device comprising:
a reception unit that receives, in a case where an ophthalmic apparatus that is one of the ophthalmic apparatuses is in contact with the PDA device, or in a case where an ophthalmic apparatus that is one of the ophthalmic apparatuses is not in contact with the PDA device and becomes spaced apart from the PDA device by a distance smaller than a predetermined distance, a state-confirmation signal from the one of the ophthalmic apparatuses, and receives from the one of the ophthalmic apparatuses a moving image signal indicating a moving image, of the eye to be examined, obtained through the examination;
a display control unit that causes the display unit to display the moving image.

16. The PDA device according to claim 15, further comprising:
a detection unit that detects one of the ophthalmic apparatuses that is either in contact with the PDA device or spaced apart from the PDA device by a distance smaller than a predetermined distance,
wherein, when the one of the ophthalmic apparatuses has been detected by the detection unit, the display control unit causes the display unit to display a screen related to the one ophthalmic apparatus.

17. The PDA device according to claim 16,
wherein the PDA device is capable of communicating with a plurality of the ophthalmic apparatuses,
wherein the PDA device further comprises a detection unit that detects one of the plurality of ophthalmic apparatuses, the detected ophthalmic apparatus being located closer to the PDA device than the other ophthalmic apparatuses, and
the display control unit causes the display unit to display a screen related to the ophthalmic apparatus detected by the detection unit.

18. The PDA device according to claim 16,
wherein the display control unit causes the display unit to display the screen that contains a moving image based on a moving image signal of the to-be-examined eye obtained by the ophthalmic apparatus detected by the detection unit and an eye-examination control information item based on an eye-examination control signal obtained by the ophthalmic apparatus detected by the detection unit.

19. The PDA device according to claim 18,
wherein the eye-examination control signal includes at least one of a set-value information item related to the examination, an eye-examination-mode-state information item related to the examination, an information item regarding left and right eyes each of which is the eye to be examined, an information item regarding a presence or absence of an eye-examination error related to the examination, and an eye-examination-result information item based on the eye-examination-result signal representing results of the examination.

20. The PDA device according to claim 16,
wherein, when one of the ophthalmic apparatuses has been detected by the detection unit, the display control unit switches a screen to be displayed by the display unit from a screen regarding awaiting patients to a screen related to the ophthalmic apparatus.

* * * * *